(12) United States Patent
McMorrow

(10) Patent No.: US 7,214,184 B2
(45) Date of Patent: May 8, 2007

(54) LARYNGOSCOPE

(76) Inventor: Roger McMorrow, 33 Lonnox St, Portobello Dublin 8 (IE)

( * ) Notice: Subject to any disclaimer, the term of this patent is extended or adjusted under 35 U.S.C. 154(b) by 0 days.

(21) Appl. No.: 10/516,806

(22) PCT Filed: Nov. 12, 2002

(86) PCT No.: PCT/EP02/12619

§ 371 (c)(1),
(2), (4) Date: Jun. 13, 2005

(87) PCT Pub. No.: WO03/041570

PCT Pub. Date: May 22, 2003

(65) Prior Publication Data

US 2005/0234303 A1    Oct. 20, 2005

(30) Foreign Application Priority Data

Nov. 13, 2001  (GB) ................................ 0127130.3

(51) Int. Cl.
*A61B 1/267*    (2006.01)

(52) U.S. Cl. ...................... 600/185; 600/131; 600/188; 600/189

(58) Field of Classification Search ................ 600/185, 600/188, 189, 190, 210, 235, 237, 245–248
See application file for complete search history.

(56) References Cited

U.S. PATENT DOCUMENTS

| | | | | |
|---|---|---|---|---|
| 1,945,380 A | * | 1/1934 | Russell | ........................ 600/189 |
| 3,643,654 A | * | 2/1972 | Felbarg | ........................ 600/189 |
| 3,870,037 A | * | 3/1975 | Cadariu et al. | ............. 600/189 |
| 3,884,222 A | * | 5/1975 | Moore | ........................ 600/188 |
| 4,360,008 A | | 11/1982 | Corazzelli | |
| 5,349,943 A | * | 9/1994 | Ruiz | .......................... 600/189 |
| 6,135,948 A | | 10/2000 | Lee | |

FOREIGN PATENT DOCUMENTS

| | | | |
|---|---|---|---|
| DE | 29502902 U1 | * | 7/1996 |
| GB | 2258398 | | 10/1993 |

\* cited by examiner

*Primary Examiner*—Linda C. M. Dvorak
*Assistant Examiner*—Matthew J. Kasztejna
(74) *Attorney, Agent, or Firm*—Porter, Wright, Morris & Arthur LLP

(57) ABSTRACT

One aspect of the present invention provides a laryngoscope comprising a blade; a doployable mirror, and an operating mechanism, the operating mechanism being arranged to deploy the mirror. The mirror is pivotable with respect to the blade and the arrangement is such that an initial operation of the operating mechanism causes the mirror to be deployed while further operation of the operating mechanism causes the mirror to be pivoted with respect to the blade. In the preferred embodiment, the blade has a pivotable tip which is also operable by the operating mechanism. The deployment of the mirror, the pivoting of the mirror 30 and the pivoting of the tip 18 can all be performed by operation of a single operating mechanism, preferably in the form of a simple lever. The laryngoscope may therefore readily be operated using only one hand and without the need for any dextrous finger movements.

24 Claims, 5 Drawing Sheets

LARYNGOSCOPE

FIELD OF THE INVENTION

The present invention relates to a laryngoscope, and in particular a laryngoscope which includes a deployable mirror.

BACKGROUND TO THE INVENTION

Intubation is a common requirement for anaesthesia, and a laryngoscope is a commonly used instrument for visualizing the larynx to allow the introduction of an endotracheal (ET) tube. The view obtained at laryngoscopy is normally graded on a 1–4 scale, depending on to what extent the view is obscured. Grades 1 and 2 usually provide little difficulty with intubation. However a grade 3 larynx can present considerable difficulty, often requiring special techniques such as blind insertion of the ET tube. A grade 4 larynx is often impossible to intubate using a standard laryngoscope and normally requires the use of more specialized equipment such as fiberoptic equipment. There are four main anatomical factors that contribute to confound the view of the larynx, namely, forward displacement of the larynx, forward or prominent upper teeth, backward displacement of the tongue and poor mouth opening. Another major factor that contributes to confound the view is the inability to achieve what is commonly known as the Magill position of neck flexion and head extension due to either cervical spine instability or pathological disease such as rheumatoid conditions or ankylosing spondylitis.

In its basic form, a laryngoscope includes a handle with a slightly curved or straight plate, commonly known as a blade, extending substantially perpendicularly from the handle. The Macintosh laryngoscope, which normally has a slightly curved blade, is an example of such a laryngoscope, In use, the blade is inserted into the patient's mouth until its tip is located at the base of the patient's tongue, Normally the tip of the blade is positioned between the base of the person's tongue and the epiglottis such that, by lifting the laryngoscope anteriorly, the tongue and epiglottis are moved allowing a clearer view of the trachea. A user will generally look for the larynx (vocal cords) which gives, an exact indication of the position in which to place the breathing tube.

The use of a curved Macintosh blade laryngoscope in the context of a Grade 3 or 4 larynx may necessitate a forward and upward levering movement. In such situations the patient's teeth may inadvertently be used as a fulcrum and persistent attempts to elevate the epiglottis frequently results in damage to the upper teeth. In an attempt to overcome this problem, a levering laryngoscope, commonly known as the McCoy laryngoscope, was created. The McCoy laryngoscope has a pivotable tip at the end of the blade, the tip being operable by a lever on the handle of the laryngoscope. When the handle is depressed, the tip pivots to pull the epiglottis away from the mouth of the larynx. The McCoy laryngoscope helps to improve the view of the larynx and, because the fulcrum point is at the distal end of the blade, decreases the likelihood of the patient's teeth being damaged.

It is also known to provide the blade with a deployable mirror which, during use, allows the user to view the larynx more clearly. U.S. Pat. No. 6,135,948 (Lee) describes an example of such a laryngoscope. However, the Lee Laryngoscope is considered to be awkward to use.

Despite the devices described above, intubation remains difficult in many cases. It would be desirable, therefore, to provide an improved laryngoscope, particularly since prolonged attempts at laryngoscopy often result in injury, most commonly vocal cord haematoma and mucosal lacerations.

SUMMARY OF THE INVENTION

A first aspect of the present invention provides a laryngoscope comprising a blade; a deployable mirror; and an operating mechanism, the operating mechanism being operatively associated with the mirror for the deployment thereof, wherein the mirror is pivotable with respect to the blade, the association of the operating mechanism and the mirror being such that an initial operation of the operating mechanism causes the mirror to be, deployed, and further operation of the operating mechanism causes the mirror to be pivoted with respect to the blade.

Preferably, the mirror is pivotably mounted on a deployment assembly, the deployment assembly being pivotably mounted on the blade, the arrangement being such that said initial operation of the operating mechanism causes the deployment assembly to be pivoted with respect to the blade, and said further operation of the operating mechanism causes the mirror to be pivoted with respect to the deployment assembly, More preferably, the deployment assembly comprises a deployment arm coupled to a secondary arm so as to permit relative movement between the deployment arm and secondary arm, the mirror being coupled to both the deployment arm and the secondary arm so that relative movement thereof causes the mirror to pivot.

Further preferably, the coupling of the deployment arm and the secondary arm includes a spring assembly biased to maintain the deployment arm and the secondary arm in a first position relative to one another, the arrangement being such that, during said initial operation of the operating mechanism, the spring assembly maintains the deployment arm and the secondary arm in the first position, and that, during said further operation of the operating mechanism, a portion of the deployment arm abuts against the blade so that the action of the operating mechanism on the deployment assembly overcomes the bias of the spring mechanism to cause relative movement of the deployment arm and the secondary arm.

Preferably, the spring assembly comprises a pin slidably located within a slot, and a spring arranged to act on the pin to maintain the pin in the first position within the slot.

Preferably, the operating mechanism comprises a lever, the lever being pivotable with respect to the blade.

Preferably, the blade extends, during use, substantially perpendicularly from a handle. More preferably, the blade is detachably mountable on the handle.

In the preferred embodiment, the lever is spring biased in a direction generally away from the handle and wherein said initial and further operation or the lever involve movement of the lever in a direction generally towards the handle.

Preferably, the mirror is actuatable between a non-deployed state, in which the mirror is located against or adjacent the blade, and at least one deployed state in which the mirror is spaced-apart from the blade with its reflective surface facing generally towards the blade. More preferably, the lever is arranged to adopt a rest state in the absence of external forces, in which rest state the lever is spaced-apart from the handle, the arrangement being such that, when the lever adopts the rest state, the mirror adopts the non-deployed state, initial movement of the lever from the rest state towards the handle causing the mirror to be deployed, and further movement of the lever towards the handle causes the mirror to be pivoted.

In the preferred embodiment, the blade comprises a pivotable tip, the operating mechanism being operatively associated with the tip to cause the tip to pivot with respect to the blade. Preferably, the operating mechanism is arranged to cause the tip to pivot during said initial operation and said further operation.

Preferably, the blade carries a light source arranged to irradiate the mirror when deployed.

A second aspect of the invention provides a blade for a laryngoscope, the blade comprising a deployable mirror; and an operating mechanism, the operating mechanism being operatively associated with the mirror for the deployment thereof, wherein the mirror is pivotable with respect to the blade, the association of the operating mechanism and the mirror being such that an initial operation of the operating mechanism causes the mirror to be deployed, and further operation of the operating mechanism causes the mirror to be pivoted with respect to the blade.

Other advantageous aspects and features of the invention will became apparent to those ordinarily skilled in the art upon review of the following description of a specific embodiment of the invention and with reference to the accompanying drawings.

BRIEF DESCRIPTION OF THE DRAWINGS

A specific embodiment of the invention is now described, by way of example, and with reference to the accompanying drawings, in which.

DETAILED DESCRIPTION OF THE DRAWINGS

Figure 1:
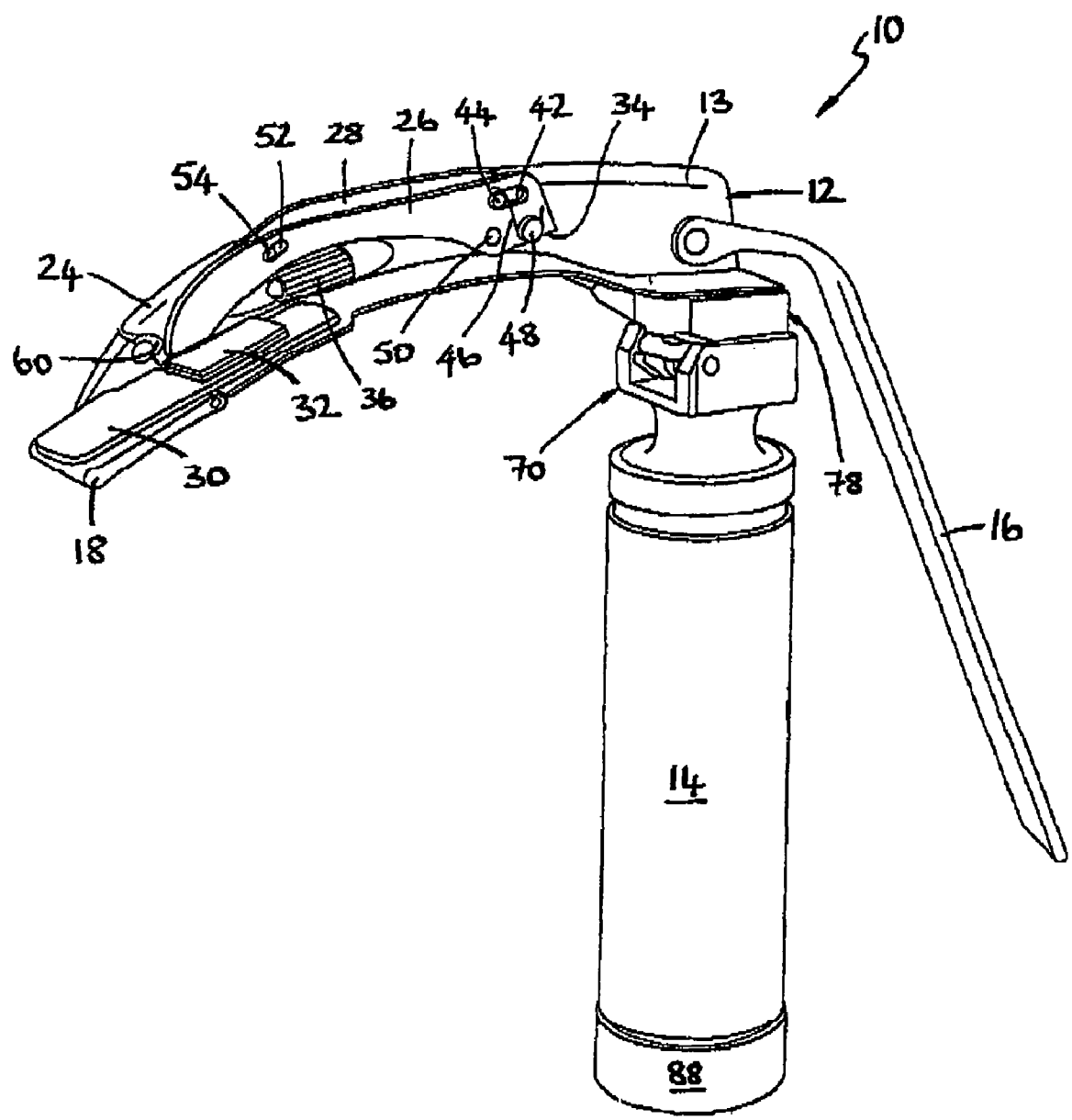
FIG. 1 is a perspective view of a preferred embodiment of a laryngoscope according to the present invention, with a mirror shown in a non-deployed state.

Referring now to the accompanying drawings, there is shown, generally indicated as 10, a preferred embodiment of a laryngoscope according to the invention The laryngoscope 10 comprises a plate, or blade 12, and a handle 14. The blade 12 is mountable on the handle 14 such that the blade 12 extends substantially perpendicularly therefrom. The blade 12 carries a mirror 30 which may be deployed and-pivoted relative to the blade 12, as will he described in detail hereinafter.

The blade 12 comprises a base plate 22 and a side flange or wall 24 extending substantially perpendicularly from the base plate 22. The blade 12 has a proximal end 13 at which, in use, the blade 12 is connected to the handle 14, and a distal end, or tip 18, which, in use, is inserted into a patient's mouth (not shown) and used in normal manner to facilitate visualization of the trachea or larynx. Preferably, the blade 12 is slightly curved in a manner similar to that of the Macintosh-type laryngoscope. At its proximal end 13, the blade 12 is provided with a mount 78 which permits the blade 12 to be releasably secured to the handle 141, by means of a corresponding interengagable coupling 70 located at the top of the handle 14. Preferably, a light source, conveniently in the form of a light bulb 36, is provided on the blade 12. Conveniently, the light 36 is mounted on the side wall 24 at a forward position on the blade 12, the light 36 being arranged, in use, to irradiate thee region around the tip 18 of the blade 12. The handle 14 is conveniently arranged to house batteries 90 in order to supply power to the light 36, although any other suitable power source may be employed. The configuration and operation of the light 36 will be described in greater detail hereinafter.

Figure 4:
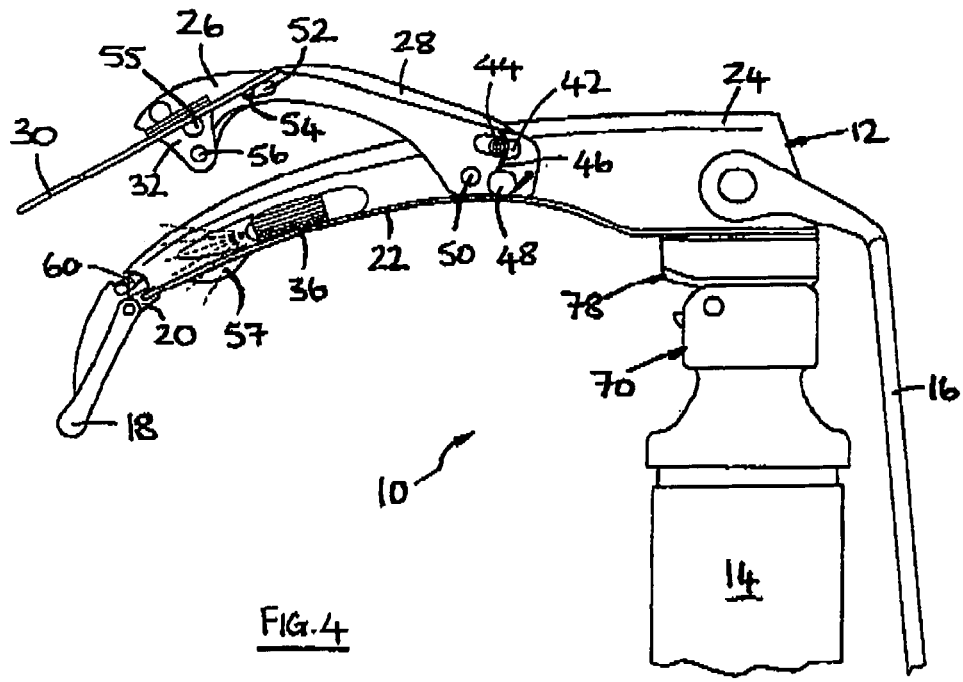
FIG. 4 is a side view of the laryngoscope of FIG. 1 with the mirror in a deployed state.
Figure 5:
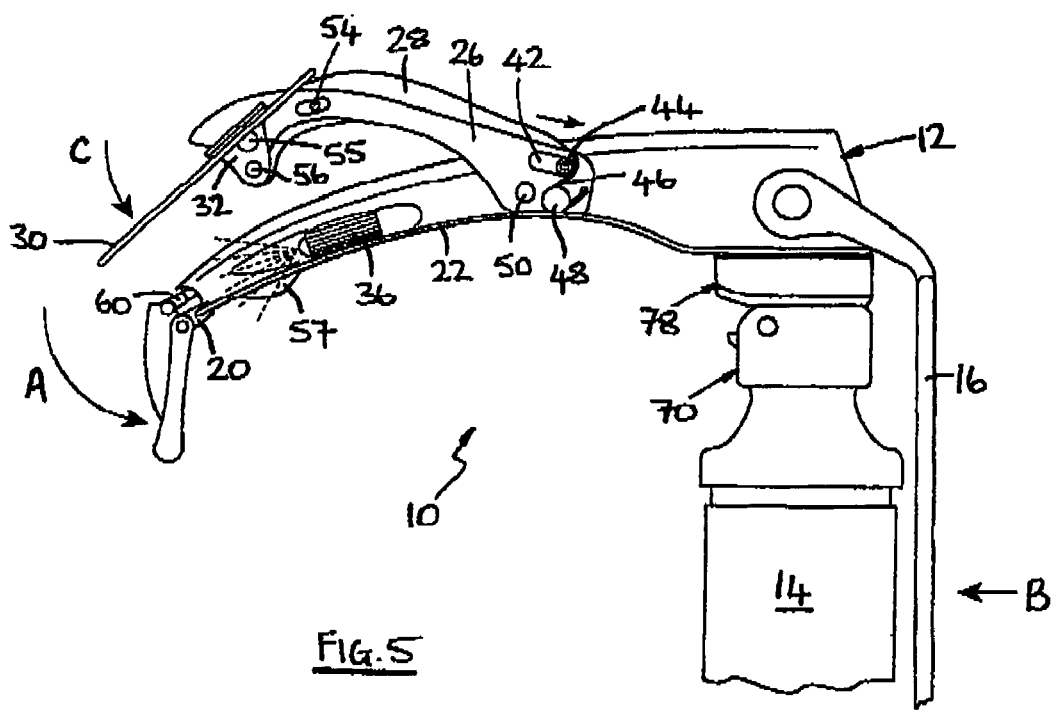
FIG. 5 is a side view of the laryngoscope of FIG. 1, similar to that shown in FIG. 4, wherein the mirror is in a different deployed state.

In the preferred embodiment, the tip 18 is pivotally mounted on the blade 12, conveniently via a link 20. As is best illustrated in FIGS. 4 and 5, the tip 18 is pivotable in the general direction of the handle 14 (as indicated by arrow A in FIG. 5) in order to draw the epiglottis (not shown) away from the laryngeal inlet of the patient, so as to provide a clearer view of the patient's larynx. In order to effect this pivoting motion, the laryngoscope 10 is provided with an operating mechanism in the form of a lover 16 which is pivotally mounted on the blade 12. In the illustrated embodiment, and in particular from FIG. 2, it can be seen that the lever 16 is mounted to the side wall 24 of the blade 12. To this end the lever 16 is connected to a bushing 66, which is seated on and is rotatable about a boss 68 which is provided on the blade 12. The bushing 66 is coupled to the boss 68 by a spring (not shown), the spring being biased to urge the bushing 66 to rotate in a clockwise direction (as viewed in FIG. 2) about the boss 68. Thus, the bushing 66, the boss 68 and the spring together serve as a spring mechanism biased to urge the lever 16 away from the handle 14. FIG. 1 shows that lever 16 in a rest state which it adopts under the action of the spring mechanism and in the absence of any external forces, such as a user's grip, being exerted.

The bushing 66 is provided with a first lug 62, to which is pivotably mounted one end of a rigid strut or rod 60. The other end of the rod 60 is pivotably connected to the tip 18 of the blade 12. The arrangement is such that depression or the lever 16 towards the handle 14 (in the direction indicated by arrow B in FIG. 5), causes the first lug 62 to move generally towards the tip 18 and this, in turn, actuates the rod 60 outwardly towards the tip 18. As the rod 60 is actuated outwardly, it causes the tip 18 to pivot with respect to the blade 12 in a direction generally towards the handle, i.e. clockwise as viewed in FIG. 2. It will be understood that the amount by which the lever 16 is depressed determines that amount by which the tip 18 is pivoted. When the lever 16 is released it will, under the action of the spring mechanism, return to its rest state thereby drawing the tip 18 back into normal alignment with the blade 12 as is shown in FIG. 1.

The mirror 30 may be actuated between a non-deployed state (as shown in FIG. 1) and at least one deployed state. FIGS. 2 to 5 illustrate the mirror 30 in various states of deployment.

In the preferred embodiment, the non-deployed state corresponds with the lever 16 adopting its rest state, as shown in FIG. 1. In this state, the mirror 30 rests against the base plate 22 of the blade 12, with the reflective surface of the mirror 30 facing towards the base plate 22. In this state, the overall size of the blade 12 (including the mirror 30) is minimized and this facilitates insertion of the blade 12 into a patient's mouth/throat (not shown). As can best be seen from FIG. 1 and FIG. 3, it is preferred that that at least the portion of the base plate 22 (including the tip 18) that receives the mirror 30 in the non-deployed state is at least as wide as the mirror 30 such that, when in the non-deployed state, the underside (i.e. reflective surface) of the mirror 30 is fully occluded by the base plate 22/tip 18. This helps to prevent the reflective surface of the mirror 30 from becoming smudged or otherwise obscured during insertion of the blade 12 into a patient's mouth. In addition, the mirror receiving portion of the tip 18 and the base plate 22 may be recessed by approximately the depth of the mirror 30 so that the mirror 30, when in the non-deployed state, sits within the recess (not shown) such that the exposed face of the mirror 30 lies flush with the base plate 22.

Once the blade 12 is inserted into a patient's mouth, it is necessary to deploy the mirror 30 in order to provide a clear view of the patient's larynx. To this end, the mirror 30 is carried by a deployment assembly which comprises a deploying arm 26 and a secondary arm 28. The deploying arm 26 is pivotably mounted on the blade 12. In the illustrated embodiment, the deploying arm 26 is pivotably mounted on the side wall 24 via a first pivot 50, and carries a spring 46 which is secured to the deploying arm 26 around an anchor 48. The secondary arm 28 is coupled to the deploying arm 26 by means of a main slot 42 in which there is located a main pin 44, and advantageously also a guide slot 52 in which there is located a guide pin 54. The arrangement is such that the deploying arm 26 and the secondary arm 28 are capable of sliding movement relative to one another in a direction generally parallel with their longitudinal axes, the extent of the sliding movement being limited by the relative dimensions of the slots 42, 52 and pins 44, 54. In the illustrated embodiment, the main slot 42 and the guide slot 52 are formed in the deployment arm 26 while the main and guide pins 44, 54 are provided on the secondary arm 26. It will be understood however that in an alternative embodiment the slots/pins may be provided on either arm 26, 28.

The spring 46 engages with and acts upon the main pin 44 so as to urge the main pin 44 towards one end of the main slot 42. In the illustrated embodiment, the spring 46 urges the main pin 44 towards the mirror-end of the main slot 42, namely the end nearest the mirror 30. The arrangement is such that, when the mirror 30 is in the non-deployed state, the spring 46 holds the main pin 44 in a first position in the slot. Conveniently, in the first position, the main pin 44 is held in engagement with the mirror-end of the slot 42 as shown in FIG. 1. Hence, the spring 46, the main slot 42 and the main pin 44 together form a spring assembly biased to maintain the deployment arm 24 and the secondary arm 26 in the first position. The guides pin 54 adopts a corresponding first position within the guide slot 52.

In order to actuate the deployment assembly, a second lug 64 is provided on the bushing 66, generally oppositely disposed on the bushing 66 with respect to the first lug 62. Thus, when the lever 16 is depressed towards the handle 14, the second lug 64 moves generally away from the tip 18 of the blade 18 (anti-clockwise as viewed in FIG. 2). A tie 58, shown in the form of a second rigid rod, has one end pivotably connected to the second lug 64. The other end of the tie 58 is connected to the deployment assembly. In the preferred embodiment, the tie 58 is connected directly to the second arm 28 and an access slot 41 is formed in the side wall 24 of the blade 12 through which the tie 58 passes.

The arrangement is such that, initial depression of the lever 16 from its rest state draws the tie 58 rearwardly (i.e. away from the tip 18), thereby exerting a rearward force on the secondary arm 28. Initially, the spring 46 acts to prevent relative sliding movement between the secondary arm 28 and the deploying arm 26. Hence, the force applied to the secondary arm 28 by the tie 58 causes the deploying arm 26 (and therefore also the secondary arm 28) to pivot about the first pivot 50 (anti-clockwise as seen from FIG. 2), thereby drawing the mirror 30 upwardly away from the base plate 22 into a deployed state. However, as can be seen from FIG. 1, the deploying arm 26 is provided with a shoulder 34 which, after limited rotation of the deploying arm 26 about pivot 50, abuts against the base plate 22. At this point, the deploying arm 26 cannot rotate any further in the direction away from the blade 12. Thus, the force exerted on the secondary arm by further rearward movement of the tie 58, due to further depression of the lever 16, overcomes the force of the spring 46 which is no longer able to hold the main pin 44 in its first position. As can best be appreciated from FIG. 4, the main pin 44 is thus drawn rearwardly within the main slot 42 (i.e. away from the mirror-end), against the action of the spring 46, resulting in relative sliding movement between the deploying arm 26 and the secondary arm 28. The laryngoscope 10 is arranged to translate this relative movement into pivoting movement of the mirror 30 relative to the deploying arm 26, as is described below.

The mirror 30 is pivotably mounted on the deployment assembly. To this end, the mirror 30 is; fixed to a mounting bracket 32 which is pivotably mounted on the deploying arm 26 at a second pivot 55. The secondary arm 28 is pivotably connected to the mounting bracket 32 at a third pivot 56 which in eccentrically located relative to the second pivot 55, as may best be seen in. FIGS. 4 and 5. The arrangement is such that, as the secondary arm 28 is drawn rearwardly (i.e. away from the mirror 30) with respect to the deploying arm 26, the mounting bracket 32 will be caused to pivot about the second pivot 55 (in an anti-clockwise direction as viewed in FIGS. 4 and 5), thereby imparting a corresponding pivoting motion to the mirror 30 (as, indicated by arrow C in FIG. 5). It will be apparent that the mounting bracket 32 could be formed integrally with the mirror 30, thereby obviating the need for the two components to be manufactured separately and subsequently secured together.

Figure 3:
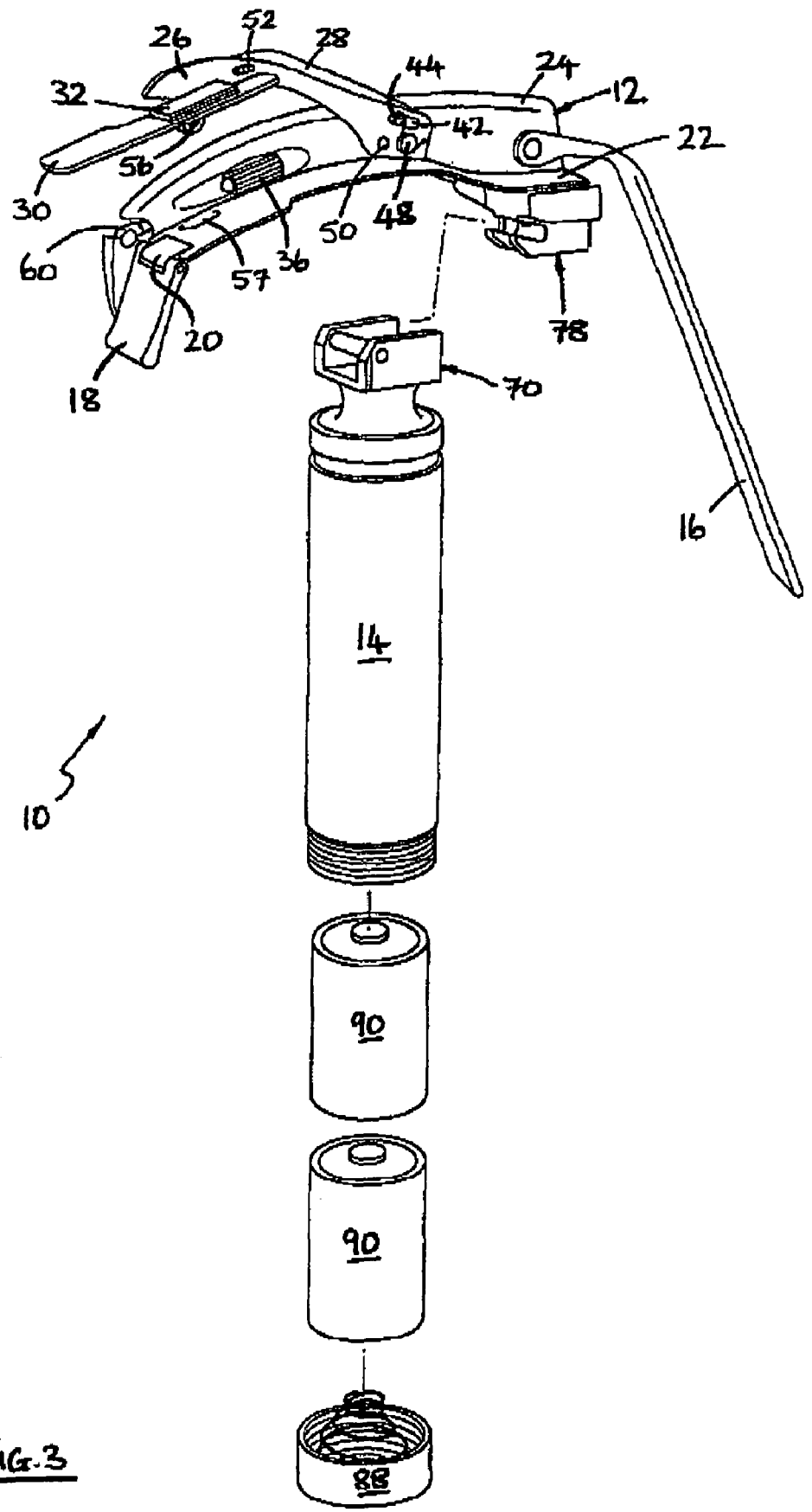
FIG. 3 is an exploded perspective view of the laryngoscope of FIG. 1.

In FIG. 3, the mirror 30 is shown in a deployed but non-pivoted position with respect to the deployment arm 26 and this corresponds to the situation where the main pin 44 (and therefore the guide pin 54) are held in the first position, i.e. no relative sliding movement of the deployment arm 26 and the secondary arm 28 has taken place. In FIG. 4, the main pin 44 is shown drawn partially back along the length of the main slot 42, and thus the mirror 30 in pivoted, or angularly displaced, with respect to the deploying arm 26 by a corresponding amount. In FIG. 5, the lever 16 has been sufficiently depressed that the main pin 44 is drawn fully back within the main slot 42, and thus the mirror 30 is in its fully pivoted, or moot angularly displaced, state with respect to the deploying arm 26.

It will be appreciated that, depending on the amount by which the lever 16 is depressed, the mirror 30 may adopt a plurality of different deployed states and that, when deployed, the mirror 30 may further adopt a plurality of different pivoted states with respect to the deployment arm 26, Hence, during use, a user is able to adjust the position and orientation of the mirror 30 until an optimal view of the larynx is obtained.

It will be apparent that, as both the lever 16 and the main pin 44 are spring biased, release of the lever 16 will result in the mirror 30 returning to its non-pivoted state, and subsequently in pivoting of the deploying arm 26 and the secondary arm 28 back towards the base plate 22, so as to return the mirror 30 to its non-deployed state.

The base plate 22 is provided with a recess 57 arranged to house the mounting bracket 32 when the mirror 30 is in the non-deployed state. Although a suitably shaped aperture (not shown) could have alternatively been provided in the base plate 22 for receiving the mounting bracket 32, the recess 57 ensures that, during insertion of the blade 12 into a patient's mouth, the mirror 30 is not contacted by saliva or the live, which may subsequently impair the view provided by the mirror 30. Further, by surrounding the mounting bracket 32 the recess 57 protects the patient's mouth and tongue from damage which may otherwise be caused during insertion of the blade 12.

In addition, the side wall 24 may be laterally recessed along at least part of the length thereof adjacent the deploying arm 26 and the secondary arm 28, such that the outwardly facing surface of the deploying arm 26 lies substantially flush with the remainder of the side wall 24. It will be appreciated that such an arrangement would provide a clearer view, in use, down the length or the blade 12.

Figure 2:
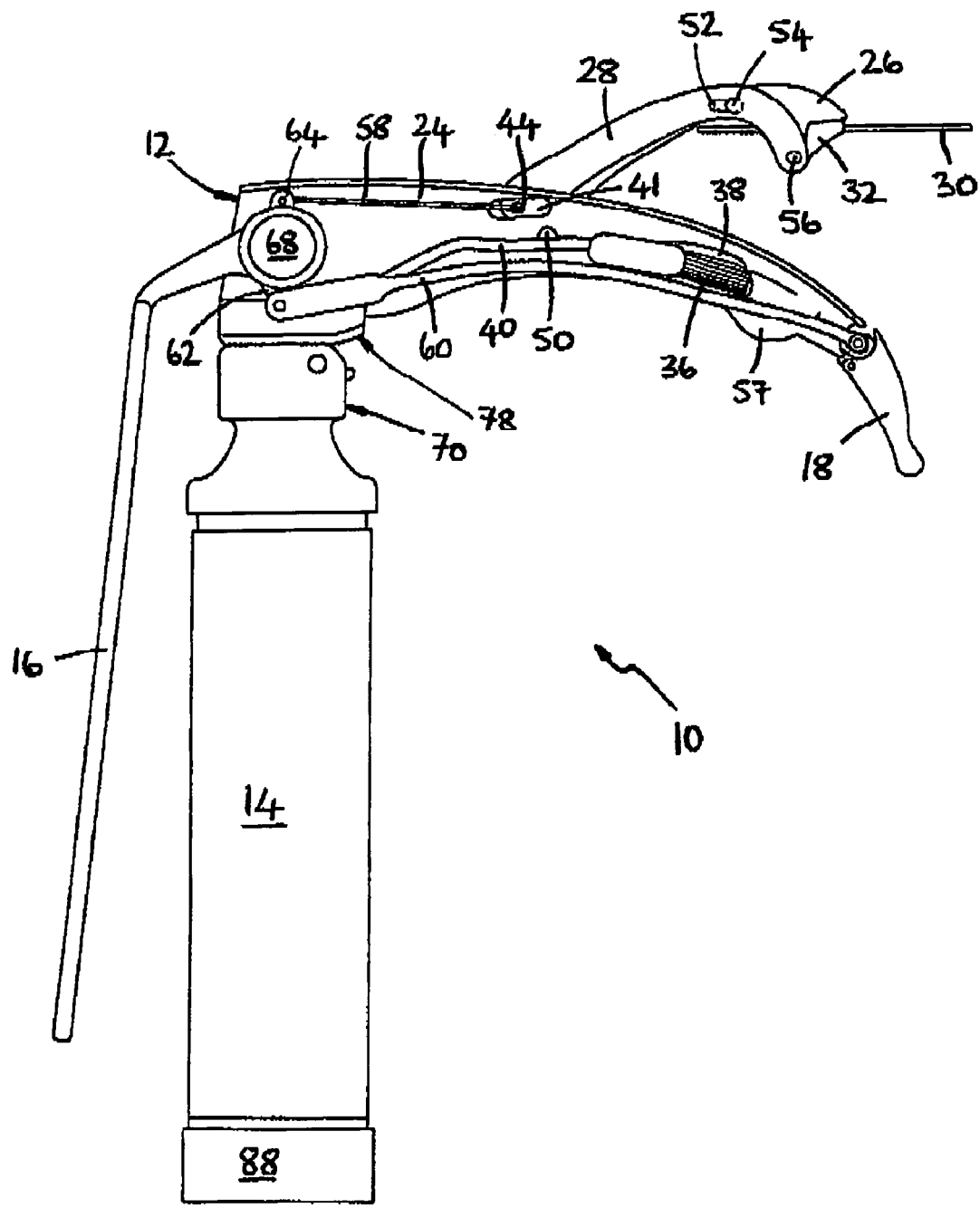
FIG. 2 is a side elevation of the laryngoscope of FIG. 1, with the mirror shown in a deployed state.
Figure 7:
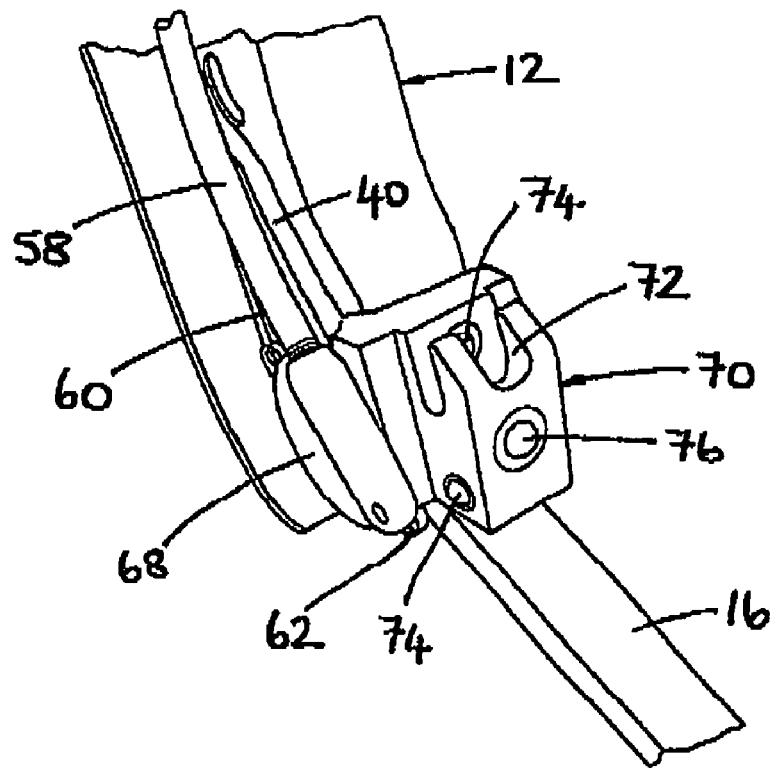
FIG. 7 shows a perspective view of part of the blade of the laryngoscope, in particular showing a coupling which permits the blade to be secured to the handle.

The light 36 is arranged to irradiate the mirror 30 when deployed. The light 36 may be of any suitable form, for example an LED, a tungsten filament bulb, or a fibre optic bundle. In order to supply the light 36 with power, a conduit 40 is connected to the light 36, and extends rearwardly to the coupling 70, as can be seen in FIG. 2 and FIG. 7. The coupling 70, during use, is electrically connected to the handle 14 so as to enable the passage of currant from the batteries 90 in the handle 14 to the conduit 40, a preferred arrangement for which is described below.

Figure 6:
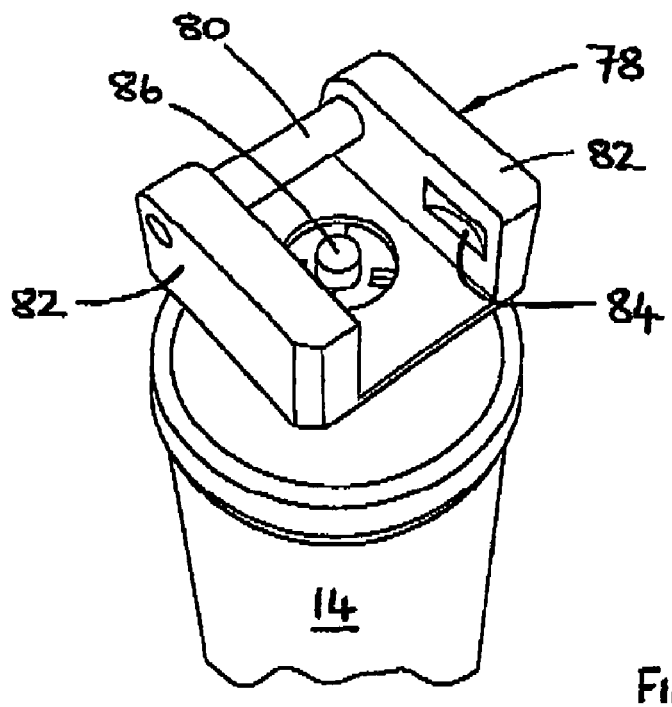
FIG. 6 is a perspective view of part of a handle forming part of the laryngoscope of FIG. 1.

The batteries 90 are inserted, by removal of a cap 88, into the handle 14. The coupling 70 at the top of the handle 14, 45 shown in FIG. 6, includes a first contact 86 projecting therefrom. When the mount 78 is secured to the coupling 70, the first contact 86 abuts a second contact 76, which is electrically connected to the conduit 40. In order to releasably secure the blade 12 to the handle 14, the coupling 70 includes a mouth 72 which engages a bar 80 of the mount 78. The coupling 70 further includes a number of conventional detent balls 74 which engage corresponding indents 84 in a pair of walls 82 of the mount 78. The coupling 70 may thus be clipped and unclipped to the mount 78, thereby supplying power to the light 36 when the handle 14 is secured to the blade 12.

With the laryngoscope 10, the deployment of the mirror 30, the pivoting of the mirror 30 and the pivoting of the tip 18 can all be performed by operation of a single lever 16. Deployment of the mirror 30 occurs simultaneously with pivoting of the tip 18 as the lever 16 undergoes initial depression from its rest state. In the preferred embodiment, the arrangement is such that the lever 16 continues to cause the tip 18 to pivot as the lever 16 is further depressed, i.e. the tip 18 pivots simultaneously with the pivoting of the mirror 30. It is found that during said further depression of the lever 16 the user can fine tune the orientation of the mirror 30 and tip 18 so as to optimize his view of the trachea/larynx. Hence, the user has full operational control over the laryngoscope 10 using only one lever 16. The laryngoscope 10 may therefore readily be operated using only one hand.

Moreover, the lever 16 may be operated by exerting a simple squeezing action on the lever 16 and does not require any dextrous finger movements.

Further, the provision of a deployable and adjustable mirror allows the larynx to be visualized in difficult intubations without the need to use fiberoptic equipment (which are expensive and require considerable user training).

In alternative embodiments (not shown), the lever 16 may be replaced with any other suitable operating mechanism. For example, a cable system may be used wherein one or more cables are connected to the deployment assembly and, when used, the pivotable blade tip, for the actuation thereof. An operating knob may be provided on the cable to allow a user to push or pull the cable (s) back and forth thereby operating the mirror and tip in a similar manner to that described above.

The foregoing description is of a preferred embodiment of the invention and a skilled person will readily understand that many of the specific component parts described above may be replaced with technically equivalent parts while achieving the same technical effect. The present invention is therefore not limited to the embodiment described herein, which may be amended or modified without departing from the scope of the present invention.

The invention claimed is:

1. A laryngoscope comprising a blade; a deployable mirror, the mirror being pivotable with respect to the blade; and an operating mechanism, the operating mechanism being operatively associated with the mirror for the deployment thereof, wherein the operating mechanism is spring biased to adopt a rest state in which the mirror adopts a non-deployed state, the association of the operating mechanism and the mirror being such that an initial operation of the operating mechanism from said rest state against said spring bias causes the mirror to be deployed, and further operation of the operating mechanism from said rest state against said spring bias causes the mirror to be pivoted with respect to the blade, wherein said operating mechanism is operable between said rest state, in which said mirror adopts a non-deployed state; a first operated state, in which said mirror adopts a deployed and non-pivoted state; and a second operated state, in which said mirror adopts a deployed and pivoted state, and wherein said spring bias is arranged to urge said operating mechanism from said second operated state to said rest state through said first operated state.

2. A laryngoscope as claimed in claim 1, wherein the mirror is pivotably mounted on a deployment assembly, the deployment assembly being pivotably mounted on the blade, the arrangement being such that said initial operation of the operating mechanism causes the deployment assembly to be pivoted with respect to the blade, and said further operation of the operating mechanism causes the mirror to be pivoted with respect to the deployment assembly.

3. A laryngoscope as claimed in claim 2, wherein the deployment assembly comprises a deployment arm coupled to a secondary arm so as to permit relative movement between the deployment arm and secondary arm, the mirror being coupled to both the deployment arm and the secondary arm so that relative movement thereof causes the mirror to pivot.

4. A laryngoscope as claimed in claim 3, wherein the coupling of the deployment arm and the secondary arm includes a spring assembly biased to maintain the deployment arm and the secondary arm in a first position relative to one another, the arrangement being such that, during said initial operation of the operating mechanism, the spring assembly maintains the deployment arm and the secondary arm in the first position, and that, during said further operation of the operating mechanism, a portion of the deployment arm abuts against the blade so that the action of the operating mechanism on the deployment assembly overcomes the bias of the spring mechanism to cause relative movement of the deployment arm and the secondary arm.

5. A laryngoscope as claimed in claim 4, wherein said spring assembly comprises a pin slidably located within a slot, and a spring arranged to act on the pin to maintain the pin in the first position within the slot.

6. A laryngoscope as claimed in claim 5, wherein the slot is formed in the deployment arm and the pin is provided on the secondary arm.

7. A laryngoscope as claimed in claim 1, wherein the operating mechanism comprises a lever, the lever being pivotable with respect to the blade.

8. A laryngoscope as claimed in claim 3, wherein the operating mechanism comprises a lever, the lever being pivotable with respect to the blade, and wherein the lover is connected to the secondary arm by a tie.

9. A laryngoscope as claimed in claim 3, wherein the mirror is provided with a mounting bracket, the mounting bracket being pivotably mounted on the deployment arm, the secondary arm being pivotably connected to the mounting bracket eccentrically of the connection between the mounting bracket and the deployment arm.

10. A laryngoscope as claimed in claim 1, wherein the blade is curved.

11. A laryngoscope as claimed in claim 1, wherein the blade extends, during use, substantially perpendicularly from a handle.

12. A laryngoscope as claimed in claim 11, wherein the blade is detachably mountable on the handle.

13. A laryngoscope as claimed in claim 11, wherein the operating mechanism comprises a lever, the lever being pivotable with respect to the blade, wherein the lever is spring biased in a direction generally away from the handle and wherein said initial and further operation of the lever involve movement of the lever in a direction generally towards the handle.

14. A laryngoscope as claimed in claim 1, wherein the mirror is actuatable between a non-deployed state, in which the mirror is located against or adjacent the blade, and at least one deployed state in which the mirror is spaced-apart from the blade with its reflective surface facing generally towards the blade.

15. A laryngoscope as claimed in claim 14, wherein the operating mechanism comprises a lever, the lever being pivotable with respect to the blade, wherein the lever is spring biased in a direction generally away from the handle and wherein said initial and further operation of the lever involve movement of the lever in a direction generally towards the handle, and wherein the lever is arranged to adopt a rest state in the absence of external forces, in which rest state the lever is spaced-apart from the handle, the arrangement being such that, when the lever adopts the rest state, the mirror adopts the non-deployed state, Initial movement of the lever from the rest state towards the handle causing the mirror to be deployed, end further movement of the lever towards the handle causes the mirror to be pivoted.

16. A laryngoscope as claimed in claim 14, wherein a recess is formed in the blade for receiving the mirror when in the non-deployed state.

17. A laryngoscope as claimed in claim 1, wherein the blade comprises a pivotable tip, the operating mechanism being operatively associated with the tip to cause the tip to pivot with respect to the blade.

18. A laryngoscope as claimed in claim 17, wherein the operating mechanism is arranged to cause the tip to pivot during said initial operation.

19. A laryngoscope as claimed in claim 17, wherein the operating mechanism is arranged to cause the tip to pivot during said further operation.

20. A laryngoscope as claimed in claim 17, wherein the blade extends, during use, substantially perpendicularly from a handle, and wherein during said initial or further operation of the operating mechanism, the tip is caused to pivot in a direction generally towards the handle.

21. A laryngoscope as claimed in claim 1, wherein the blade carries a light source arranged to irradiate the mirror when deployed.

22. A blade for a laryngoscope, the blade comprising a deployable mirror, the mirror being pivotable with respect to the blade; and an operating mechanism, the operating mechanism being operatively associated with the mirror for the deployment thereof, wherein the operating mechanism is spring biased to adopt a rest state in which the mirror adopts a non-deployed state, the association of the operating mechanism and the mirror being such that an initial operation of the operating mechanism from said rest state against said spring bias causes the mirror to be deployed, and further operation of the operating mechanism from said rest state against said spring bias causes the mirror to be pivoted with respect to the blade, wherein said operating mechanism is operable between said rest state, in which said mirror adopts a non-deployed state; a first operated state, in which said mirror adopts a deployed and non-pivoted state; and a second operated state, in which said mirror adopts a deployed and pivoted state, and wherein said spring bias is arranged to urge said operating mechanism from said second operated state to said rest state through said first operated state.

23. A laryngoscope comprising a blade; a deployable mirror, the mirror being pivotable with respect to the blade; and an operating mechanism, the operating mechanism being operatively associated with the mirror for the deployment thereof, wherein the operating mechanism is spring biased to adopt a rest state in which the mirror adopts a non-deployed state, the association of the operating mechanism and the mirror being such that an initial operation of the operating mechanism from said rest state against said spring bias causes the mirror to be deployed, and further operation of the operating mechanism from said rest state against said spring bias causes the mirror to be pivoted with respect to the blade, the mirror being pivotably mounted on a deployment assembly, the deployment assembly being pivotably mounted on the blade, the arrangement being such that said initial operation of the operating mechanism causes the deployment assembly to be pivoted with respect to the blade, and said further operation of the operating mechanism causes the mirror to be pivoted with respect to the deployment assembly, the deployment assembly comprising a deployment arm coupled to a secondary arm so as to permit relative movement between the deployment arm and secondary arm, the mirror being coupled to both the deployment arm and the secondary arm so that relative movement thereof causes the mirror to pivot, wherein the coupling of the deployment arm and the secondary arm includes a spring assembly biased to maintain the deployment arm and the secondary arm in a first position relative to one another, the arrangement being such that, during said initial operation of the operating mechanism, the spring assembly maintains the deployment arm and the secondary arm in the first position, and that, during said further operation of the operating mechanism, a portion of the deployment arm abuts against the blade so that the action of the operating mechanism on the deployment assembly overcomes the bias of the spring mechanism to cause relative movement of the deployment arm and the secondary arm.

24. A laryngoscope comprising a blade; a deployable mirror, the mirror being pivotable with respect to the blade; and an operating mechanism, the operating mechanism being operatively associated with the mirror for the deployment thereof, wherein the operating mechanism is spring biased to adopt a rest state in which the mirror adopts a non-deployed state, the association of the operating mechanism and the mirror being such that an initial operation of the operating mechanism from said rest state against said spring bias causes the mirror to be deployed, and further operation of the operating mechanism from said rest state against said spring bias causes the mirror to be pivoted with respect to the blade, the mirror being pivotably mounted on a deployment assembly, the deployment assembly being pivotably mounted on the blade, the arrangement being such that said initial operation of the operating mechanism causes the deployment assembly to be pivoted with respect to the blade, and said further operation of the operating mechanism causes the mirror to be pivoted with respect to the deployment assembly, the deployment assembly comprising a deployment arm coupled to a secondary arm so as to permit relative movement between the deployment arm and secondary arm, the mirror being coupled to both the deployment arm and the secondary arm so that relative movement thereof causes the mirror to pivot, wherein the mirror is provided with a mounting bracket, the mounting bracket being pivotably mounted on the deployment arm, the secondary arm being pivotably connected to the mounting bracket eccentrically of the connection between the mounting bracket and the deployment arm.

* * * * *